US00PP27363P2

(12) United States Plant Patent
Egger

(10) Patent No.: US PP27,363 P2
(45) Date of Patent: Nov. 8, 2016

(54) ***HEUCHERA* PLANT NAMED 'TOKYO'**

(50) Latin Name: ***Heuchera* hybrid**
Varietal Denomination: Tokyo

(71) Applicant: Terra Nova Nurseries, Inc., Canby, OR (US)

(72) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 81 days.

(21) Appl. No.: 14/545,254

(22) Filed: Apr. 13, 2015

(51) Int. Cl.
*A01H 5/12* (2006.01)

(52) U.S. Cl.
USPC ..... Plt./440

(58) Field of Classification Search
USPC ..... Plt./440
See application file for complete search history.

*Primary Examiner* — June Hwu
(74) *Attorney, Agent, or Firm* — Klarquist Sparkman, LLP

(57) ABSTRACT

A new and distinct *Heuchera* plant characterized by medium size yellow-green to green leaves with a white veil, red flowers on dark scapes, a low mounding habit, and excellent vigor.

1 Drawing Sheet

Botanical denomination: *Heuchera* hybrid.
Variety designation: 'Tokyo'.

BACKGROUND

The present invention relates to a new and distinct cultivar of *Heuchera* and given the cultivar name of 'Tokyo'. *Heuchera* is in the family Saxifragaceae. *Heuchera* 'Tokyo' originated from a planned breeding program for red flowering *Heuchera*. The seed parent was *Heuchera* 'K652-1' and the pollen parent was *Heuchera* 'K680-1', both proprietary, unpatented, unreleased seedlings. The new cultivar was chosen for its vigor, lime green leaves, and showy red flowers.

Compared to the seed parent, *Heuchera* 'K652-1', the new cultivar has yellow-green to green rather than mint green leaves and a clear red rather than a dull red flower.

Compared to the pollen parent, *Heuchera* 'K680-1', the new cultivar has yellow-green to green rather than blue green leaves and a clear red rather than a burnt red flower.

There are yellow or yellow green foliage *Heuchera* with red flowers on the market. Compared to *Heuchera* 'Lipstick', U.S. Plant Pat. No. 22,093, the new cultivar has medium yellow green to green leaves with a white veil rather than small blue green leaves.

This new *Heuchera* is uniquely distinguished by:

1. medium size yellow-green to green leaves with a white veil,
2. red flowers on dark scapes,
3. a low mounding habit,
4. and excellent vigor.

This new cultivar has been reproduced only by asexual propagation (tip cuttings and tissue culture). Each of the progeny exhibits identical characteristics to the original plant. Asexual propagation 2013 by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may change with variations in environment without a change in the genotype of the plant.

BRIEF DESCRIPTION OF THE DRAWINGS

FIG. 1 shows a six-month-old plant of *Heuchera* 'Tokyo' growing in a one gallon pot outside in the shade in mid-July in Canby, Oreg.

FIG. 2 shows a three-year-old plant growing in the trial bed in the shade mid-July in Canby, Oreg.

DETAILED PLANT DESCRIPTION

The following is a detailed description of the new *Heuchera* cultivar based on observations of three-year-old specimens growing in shade in the trial bed in early September in Canby, Oreg. Canby is Zone 8 on the USDA Hardiness map. Temperatures range from a high of 95° F. in August to an average of 32° F. in January. Normal rainfall in Canby is 42.8 inches per year. The color descriptions are all based on *The Royal Horticultural Society Colour Chart, 5th* edition, 2007.

Plant:

*Form*.—Basal rosette, herbaceous perennial.
*Hardiness*.—USDA Zone 4 to 9.
*Size*.—26 cm tall from top of the foliage to the soil and 52 cm wide.
*Habit*.—Low mounding.
*Vigor*.—Excellent.

Leaf:

*Type*.—Simple.
*Arrangement*.—Rosette.
*Number*.—About 250.
*Shape*.—Broadly ovate to orbicular.
*Lobing/division*.—7 shallow lobes.
*Venation*.—Palmate.
*Margins*.—Broadly, shallowly crenate.
*Apex*.—Mucronulate.
*Base*.—Cordate, usually overlapping.

*Blade size*.—Grows to 9.5 cm long and 8.5 cm wide.
*Texture*.—Supple, leathery.
*Surface texture*.—Glandular hairs on both sides.
*Petiole description*.—Grows to 12.5 cm long and 3 mm wide, glandular hairs, Yellow Green 146B.
*Leaf color*.—Topside, spring Yellow Green 145A including veins and developing a white veil or overlay as it matures, White NN155B, bottom side Yellow Green 145A including vein; summer leaves topside with newest leaves like spring leaves but darken further along veins to Green 137B with veil White NN155B, bottom side Yellow Green 147B including veins; fall to winter leaves topside Green 137B with veil White NN155B, bottom side Yellow Green 147B including veins.

Inflorescence:
*Size*.—Grows to 5 cm wide and 12 cm long.
*Type*.—Upright thyrse.
*Number of flowers per thryse*.—50 to 100.
*Number of thyrse*.—About 40.
*Peduncle*.—Grows to 24 cm long, 3 mm wide at base, glandular hairs, Greyed Purple 187B.
*Pedicel*.—Variable in size, with glandular hairs, Greyed Purple 187B.
*Bloom period*.—July to October in Canby, Oreg.

Flower bud:
*Size*.—3 mm wide and 6 mm long.
*Description*.—Glandular puberulent, tear drop shape, side to down-facing.
*Color*.—Red 46A.

Flower:
*Type*.—Perfect.
*Shape*.—Campanulate.
*Attitude*.—Side to down-facing.
*Size*.—6 mm long and 10 mm wide.
*Corolla description*.—5 petals, 4.5 mm long and 1.5 mm wide, broadly spatulate, margins entire, tip acute, glandular hairs on both sides, both sides Red 53D blending to 53C at base.
*Calyx description*.—Campanulate, 6 mm long and 10 mm wide, with 5 lobes divided ⅕ way to the base, each 3 mm wide and 4.5 mm long, glandular hairs both sides, tips acute, margin entire; color inside — Red 51A and outside — Red 53B.
*Stamen description*.—5 in number, 2 mm long, filaments 2.5 mm long, White NN155C, anthers 0.5 mm, White NN155C, pollen none.
*Pistil description*.—1, 2-beaked, 4 mm long and 2 mm wide, Yellow Green 145D overall; ovary 2 mm long and 2 mm wide, style 2 mm long.
*Fragrance*.—None.
*Lastingness*.—Each thyrse blooms for about 4 weeks on the plant.

Fruit: None, infertile.
Seed: None.
Pest and disease tolerance: The new cultivar is typical to the genus. No problems have been found in Canby, Oreg.

I claim:

1. A new and distinct *Heuchera* plant as herein illustrated and described.

* * * * *

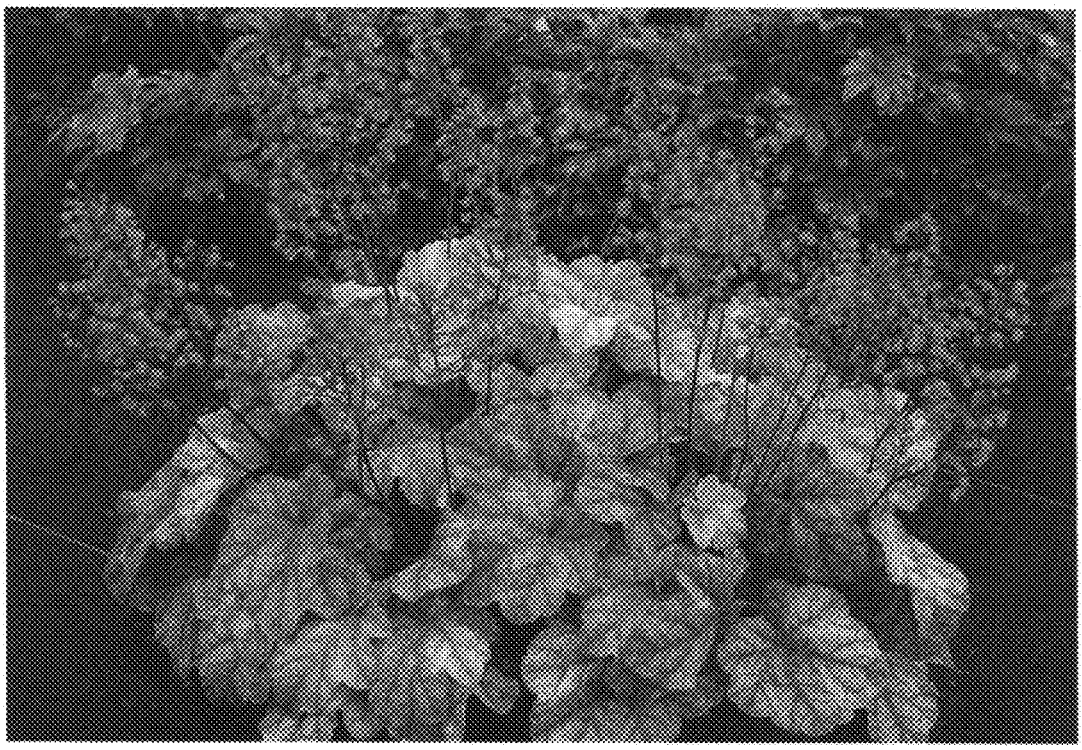

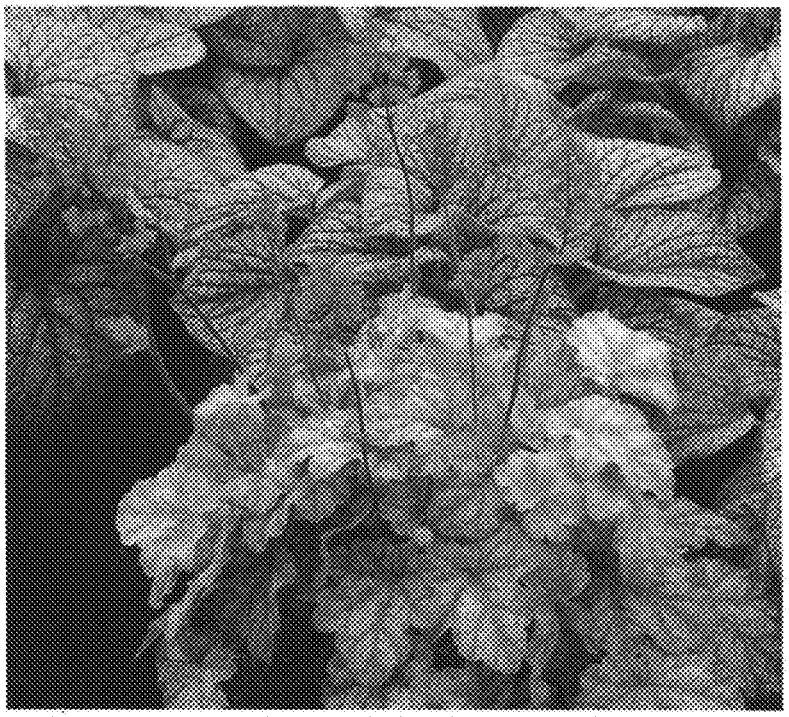
FIG. 1 above, FIG. 2 below